(12) United States Patent
Klyce et al.

(10) Patent No.: US 7,370,969 B2
(45) Date of Patent: May 13, 2008

(54) CORNEAL TOPOGRAPHY ANALYSIS SYSTEM

(75) Inventors: Stephen D. Klyce, New Orleans, LA (US); Michael K. Smolek, New Orleans, LA (US); Masanao Fujieda, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 628 days.

(21) Appl. No.: 10/813,620

(22) Filed: Mar. 31, 2004

(65) Prior Publication Data

US 2005/0225724 A1 Oct. 13, 2005

(51) Int. Cl.
*A61B 3/10* (2006.01)
*A61B 5/103* (2006.01)

(52) U.S. Cl. .............................. 351/212; 600/587
(58) Field of Classification Search ............... 351/212
See application file for complete search history.

(56) References Cited

U.S. PATENT DOCUMENTS

| 5,500,697 A | | 3/1996 | Fujieda |
| 5,796,859 A | * | 8/1998 | Mammone ............... 351/212 |
| 5,993,001 A | * | 11/1999 | Bursell et al. ............ 351/212 |
| 2002/0075451 A1 | * | 6/2002 | Ruiz ......................... 351/212 |
| 2005/0174535 A1 | * | 8/2005 | Lai et al. .................. 351/205 |

FOREIGN PATENT DOCUMENTS

JP 7-124113 A 5/1995

OTHER PUBLICATIONS

NIDEK Optical Path Difference Scanning System, "OPD-Scan" catalogue.
Michael K Smolek et al. Current Keratoconus Detection Methods Compared With a Neural Network Approach, Investigative Ophthalmology & Visual Science, Oct. 1997, vol. 38, No. 11, pp. 2290-2299.
Naoyuki Maeda, et al Automated Keratoconus Screening With Corneal Topography Analysis; Investigative Ophthalmology & Visual Science, May 1994, vol. 35, No. 6.
Tomey Topographic Modeling System TMS-1 catalogue.
Tomey Topographic Modeling System TMS-4 catalogue.

\* cited by examiner

*Primary Examiner*—Scott J. Sugarman
*Assistant Examiner*—DaWayne A Pinkney
(74) *Attorney, Agent, or Firm*—Sughrue Mion, PLLC (57) ABSTRACT

A corneal topography analysis system includes: an input unit for inputting corneal curvature data; and an analysis unit that determines plural indexes characterizing topography of the cornea based on the input corneal curvature data, the analysis unit further judges corneal topography from features inherent in predetermined classifications of corneal topography using the determined indexes and a neural network so as to judge at least one of normal cornea, myopic refractive surgery, hyperopic refractive surgery, corneal astigmatism, penetrating keratoplasty, keratoconus, keratoconus suspect, pellucid marginal degeneration, or other classification of corneal topography.

11 Claims, 7 Drawing Sheets
(1 of 7 Drawing Sheet(s) Filed in Color)

FIG. 4
(BINARY DECISION TREE IN EXPERT SYSTEM)

| | 0% | 25% | 50% | 75% | 100% |
|---|---|---|---|---|---|
| NRM | 0.0% | | | | |
| AST | 0.0% | | | | |
| KCS | 0.0% | | | | |
| KC | 99.4% KSI=93.04% | | | | |
| PMD | 0.0% | | | | |
| PKP | 0.1% | | | | |
| MRS | 0.2% | | | | |
| HRS | 0.0% | | | | |
| OTH | 0.3% | | | | |

| | | | |
|---|---|---|---|
| SRI  : 1.94 | ACP : 54.86 |
| SIMK1: 61.86 | IAI : 0.71 |
| SIMK2: 54.07 | FAA : 74.96 |
| MINK : 52.03 | KCI : 1.00 |
| OSI : 13.46 | CVP : 194.78 |
| DSI : 22.12 | SDP : 9.88 |
| CSI : 5.93 | SAI : 3.62 |
| KPI : 0.54 | CEI : 1.32 |
| CYL : 6.32 | SRC : 1.84 |

KSI = 0.0069 (SIMK1) + 0.0016 (OSI) + 0.0220 (SRI) + 0.0055 (DSI) + 0.0091 (MINK) + -0.0225 (KPI) + 0.0087 (CYL) + 0.0144 (IAI) + -0.0009 (CSI) + -0.0137 (SAI) + 0.0489 (SDP) + 0.0073 (ACP) + -0.0032 (CEI) + 0.0224 (SRC) + 0.0243 (SIMK2) + 0.0257 (CVP) + -0.0737 (FAA) + 0.0071 (KCI)

KCS = -0.2536 (OSI) + 0.6255 (DSI) + 0.6087 (KPI) + 0.0262 (CYL) + 0.1073 (IAI) + 0.5513 (CSI) + 0.4107 (SAI) + -0.2324 (SDP) + -0.1727 (CEI) + -0.5790 (CVP) + 0.0054 (KCI)

PMD = 0.1244 (SIMK1) + 0.1081 (OSI) + 0.0785 (SRI) + 0.0725 (DSI) + 0.0452 (MINK) + 0.0393 (KPI) + 0.0386 (CYL) + 0.0167 (IAI) + 0.0003 (CSI) + -0.0035 (SAI) + -0.0153 (SDP) + -0.0221 (ACP) + -0.0321 (CEI) + -0.0681 (SRC) + -0.0762 (SIMK2) + -0.1198 (CVP)

PKP = 0.0866 (SIMK1) + 0.0302 (OSI) + -0.0006 (SRI) + 0.0028 (DSI) + -0.0314 (MINK) + 0.0583 (KPI) + 0.0021 (CYL) + 0.1338 (IAI) + -0.0459 (CSI) + -0.0156 (SAI) + -0.0294 (SDP) + -0.0155 (ACP) + 0.0183 (CEI) + -0.0121 (SRC) + 0.0029 (SIMK2) + -0.0451 (CVP) + -0.0033 (FAA)

NRM = -0.1650 (SIMK1) + -0.0141 (OSI) + -0.0519 (SRI) + -0.2721 (DSI) + 0.0299 (MINK) + 0.2572 (KPI) + -0.3062 (CYL) + 0.0255 (IAI) + 0.1941 (CSI) + -0.2009 (SAI) + -0.3098 (SDP) + -0.1189 (ACP) + 0.1186 (CEI) + -0.0528 (SRC) + -0.0622 (SIMK2) + -0.3062 (CVP) + -0.0764 (FAA) + -0.1250 (KCI)

MRS = -0.0359 (SIMK1) + 0.0333 (OSI) + -0.0037 (SRI) + -0.0078 (DSI) + 0.0048 (MINK) + 0.3986 (KPI) + -0.0508 (CYL) + 0.0273 (IAI) + -0.0286 (CSI) + 0.0046 (SAI) + 0.0369 (SDP) + -0.0037 (ACP) + -0.0706 (CEI) + 0.0567 (SRC) + 0.0039 (SIMK2) + -0.0060 (CVP) + 0.0351 (FAA) + -0.0227 (KCI)

KC = 0.1655 (SIMK1) + 0.0585 (OSI) + -0.1228 (SRI) + 0.0637 (DSI) + 0.0210 (MINK) + 0.1189 (KPI) + 0.0416 (CYL) + -0.1346 (IAI) + 0.1096 (CSI) + 0.0809 (SAI) + 0.0325 (SDP) + 0.0667 (ACP) + -0.0499 (CEI) + -0.0257 (SRC) + -0.0853 (SIMK2) + 0.0298 (CVP) + -0.0237 (FAA) + 0.0096 (KCI)

HRS = -0.1336 (SIMK1) + -0.1360 (OSI) + -0.1332 (SRI) + 0.2551 (DSI) + 0.2585 (MINK) + -0.1508 (KPI) + -0.4129 (CYL) + 0.1856 (IAI) + -0.2606 (CSI) + -0.2394 (SAI) + -0.0501 (SDP) + -0.1463 (ACP) + 0.2777 (CEI) + 0.2931 (SRC) + 0.1321 (SIMK2) + -0.0815 (CVP) + 0.1675 (FAA) + -0.1375 (KCI)

AST = 0.0051 (SIMK1) + -0.0042 (OSI) + -0.0012 (SRI) + 0.0022 (DSI) + 0.0034 (MINK) + -0.0057 (KPI) + 0.0031 (CYL) + -0.0029 (IAI) + 0.0013 (CSI) + -0.0041 (SAI) + -0.0054 (SDP) + 0.0022 (ACP) + 0.0039 (CEI) + -0.0050 (SRC) + 0.0028 (SIMK2) + -0.0054 (CVP) + 0.0021 (FAA) + -0.0012 (KCI)

CORNEAL TOPOGRAPHY ANALYSIS SYSTEM

BACKGROUND OF THE INVENTION

1. Field of the Invention

The present invention relates to a corneal topography analysis system and a method of performing corneal topography analysis.

2. Description of the Related Art

Corneal topography analysis systems are known which analyze the three-dimensional topography of the cornea to be examined by projecting a number of Placido rings onto the cornea, taking the Placido ring image created by the convex surface of the cornea by means of an image sensor, and finding data for the curvature of the cornea based on the taken Placido ring image. The corneal topography is displayed in terms of various kinds of color maps. The information about the corneal topography obtained by such an analysis system is utilized for planning an operation for correcting the cornea, for planning cataract surgery, and for postoperative evaluations. In addition, the topography is used for early discovery and diagnosis of keratoconus that is one of several corneal diseases.

As a diagnosis of keratoconus, a method of judging keratoconus topography using a neural network approach is disclosed by Michael K. Smolek et al. in "Current Keratoconus Detection Methods Compared With a Neural Network Approach, Investigative Ophthalmology & Visual Science, October 1997, Vol. 38, No. 11, pp. 2290-2299" (Reference 1), which is incorporated herein by reference. In this method, the presence of keratoconus (KC) and keratoconus suspects (KCS) are judged using a neural network and 10 indexes characterizing the corneal topography, i.e., Differential Sector Index (DSI), Opposite Sector Index (OSI), Center-Surround Index (CSI), Analyzed Area (AA), Cylinder (CYL), Irregular Astigmatism Index (IAI), the steep axis of simulated keratometry (SK1), Surface Regularity Index (SRI), Surface Asymmetry Index (SAI) and the Standard Deviation of corneal Power (SDP). Conventionally, however, only keratoconus topographies have been judged. The categories of corneal topographies and the display of the results of the analysis leave room for further improvement.

The spacing and number of Placido rings are different among manufacturers of corneal topography systems for calculating the indexes that are necessary for classification of keratoconus topographies. Furthermore, the number of data items obtained by edge detection of ring images and the data structure are different among the manufacturers of the systems. Generally, therefore, there is no data comparability among the manufacturers. It follows that corneal topography is analyzed based on point data for the data structure for each individual manufacturer. In addition, even for the same manufacturer, if the Placido ring structure is varied, it is necessary to change the analysis program and display program.

SUMMARY OF THE INVENTION

It is an object of the present invention to provide a corneal topography analysis system, and a method of performing corneal topography analysis, that improves on the classifications of corneal topographies, such as keratoconus topographies, and that can diagnose them more precisely. It is another object to provide a corneal topography analysis system, and method of performing corneal topography analysis, that absorbs differences in Placido ring structure or data structure that would normally occur among different corneal topography analysis systems and which needs no amendment in subsequent analysis processing, display, and other processing.

To achieve these objectives, the present invention provides a corneal topography analysis system comprising an input unit, preferably one that can receive input from different corneal curvature measuring devices, for entering corneal curvature data, such as corneal curvature data obtained by projecting Placido rings onto a cornea and taking a Placido ring image created by the convex surface of the cornea, or by other methods for measuring corneal curvature. The system further comprises an analysis unit for determining plural indexes characterizing topography of the cornea based on the input corneal curvature data, for judging corneal topography from features inherent in predetermined classifications of corneal topography using the determined indexes and a neural network, for judging at least one of normal cornea, myopic refractive surgery, hyperopic refractive surgery, corneal astigmatism, penetrating keratoplasty, keratoconus, keratoconus suspect, pellucid marginal degeneration, or other classifications, and for judging its probability and grading the severity of keratoconus using the determined indexes. In addition, the system may comprise a display unit for displaying results of the judgments made by the analysis unit.

As an example of one particular application, the analysis unit judges keratoconus cases from similarity to keratoconus and from severity of keratoconus using the determined indexes and the neural network.

The invention also provides a corneal topography analysis system comprising an input unit, preferably one that can receive input from different corneal curvature measuring devices, for entering corneal curvature data, such as data obtained by projecting Placido rings onto a cornea and detecting a Placido ring image created by a convex surface of the cornea, or by other methods for measuring corneal curvature. This system further comprises a computational unit for converting the entered corneal curvature data into a denser first data matrix by interpolation, removing high-frequency components from resulting data by frequency analysis, and converting produced data into corneal curvature data in the form of a given second data matrix. Additionally, this system comprises an analysis unit for judging classifications of corneal topographies based on the converted corneal curvature data and a display unit for displaying results of the judgments.

Other objectives and features of the invention, including methods of carrying out the invention, will become evident in the course of the description thereof, which follows.

BRIEF DESCRIPTION OF THE DRAWINGS

The application file contains at least one drawing executed in color. Copies of this application with color drawings will be provided by the Office upon request and payment of the necessary fee.

The advantages, nature and various additional features of the invention will appear more fully upon consideration of the illustrative embodiment of the invention which is schematically set forth in the accompanying drawings.

FIG. 8 represents an example of polynomial expressions of a neural network.

DESCRIPTION OF THE PREFERRED EMBODIMENTS

Figure 1:
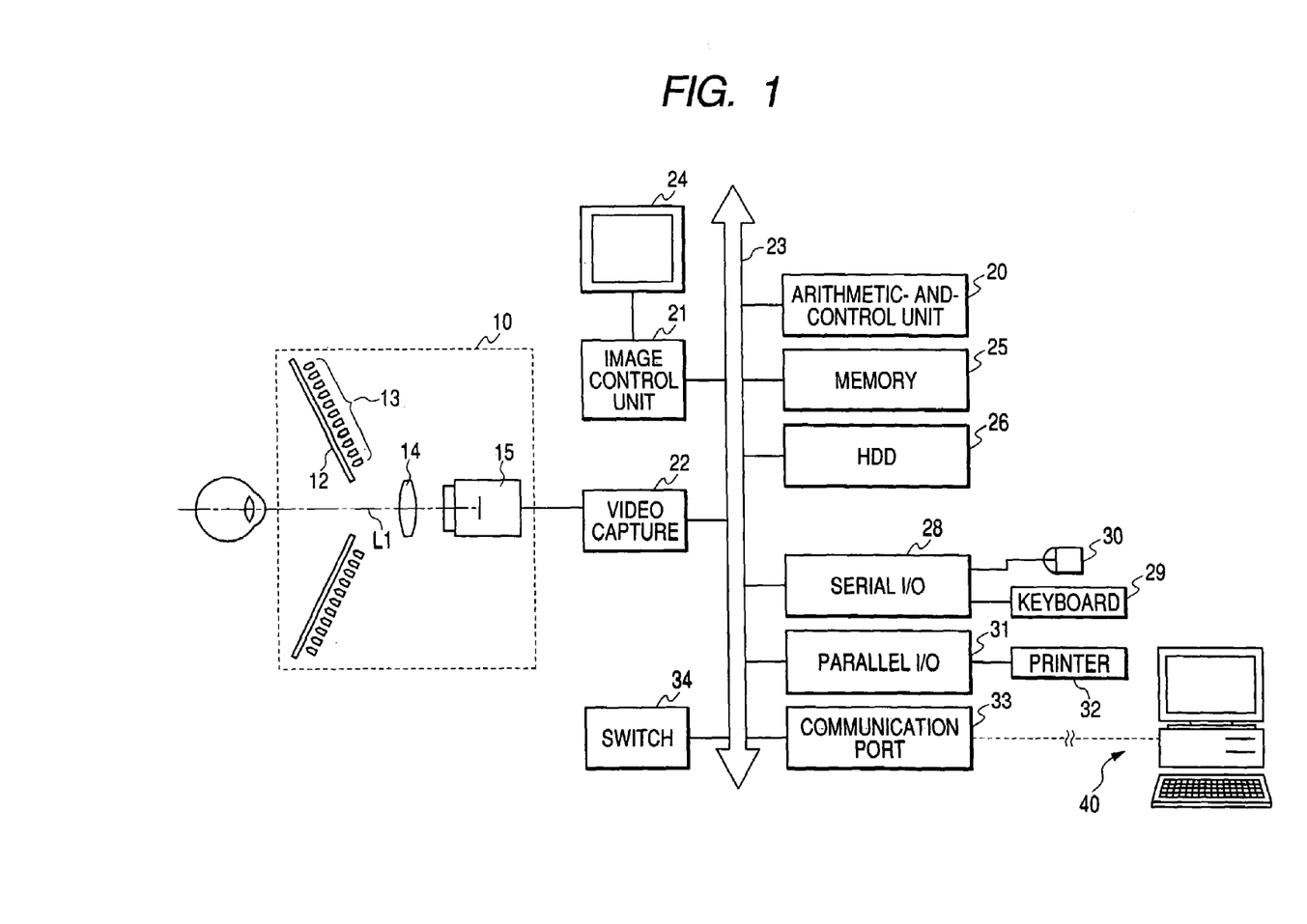
FIG. 1 is a schematic diagram of a corneal topography analysis system according to the present invention.

Preferred embodiments of the present invention are hereinafter described with reference to the drawings. FIG. 1 is a schematic diagram of a corneal topography analysis system according to the present invention. This system includes a measuring optical system 10 for measuring the corneal topography. The optical system 10 includes a Placido disk 12 on which a large number of concentric Placido rings are formed about an optical axis L1, an illumination light source 13 for substantially uniformly illuminating the ring pattern on the Placido disk 12, an objective lens 14, and a CCD camera 15. The objective lens 14 and CCD camera 15 are used to take the ring pattern image projected onto a cornea to be examined. The structure of the Placido disk 12 may be of the cone type. The objective lens 14 and CCD camera 15 act also as a viewing optical system for observing the anterior eye part of the eye examined. The topography system is fitted with a fixation optical system and an alignment optical system (not shown). Detailed descriptions of the fixation optical system and the alignment optical system are omitted, since such descriptions are not necessary for one skilled in the art to fully understand the invention.

While the measuring optical system 10 described above employs a Placido disk for measuring the corneal topography, the invention is not limited in this respect, and other corneal measuring devices may be used.

The image taken by the CCD camera 15 is accepted into a video capture device 22, which is connected with an arithmetic-and-control unit 20 via a bus 23. The arithmetic-and-control unit 20 analyzes or otherwise processes the Placido ring image taken by the CCD camera 15. An image control unit 21 is connected with a liquid crystal display 24 that can provide a color display to control the image displayed on the display 24 or that can display the results of the analysis. A memory 25 for storing the Placido ring image and the results of the analysis, a hard disk (HDD) 26 loaded with an analysis program or the like, a serial I/O 28 connected to a keyboard 29 and a mouse 30, a parallel I/O 31 connected to a printer 32, a control switch 34 having various switches, a communication port 33, and so on are connected to the bus 23. An external computer 40 can be connected to the communication port 33 through which data can be sent and received.

A method of taking the Placido ring image and subsequent analytical processing are described next. During measurement, the measuring optical system 10 is appropriately aligned with the eye to be examined. Subsequently, a trigger switch is depressed to light the light source 13. A Placido ring pattern created by the Placido disk 12 is projected onto the cornea of the eye being examined. The Placido ring pattern projected onto the examined eye is taken by the CCD camera 15. The resulting Placido ring image is stored in the memory 25. The arithmetic-and-control unit 20 detects the edges of the boundaries between black and white circles of the ring pattern from the image stored in the memory 25. The results are sent to the image control unit 21. The image control unit 21 creates and displays a Placido ring image at the corresponding edge positions of the taken ring image, the displayed image being rimmed with an easily recognizable color, which is displayed on the display 24.

If the image derived by detection of the edge positions and displayed on the display 24 is acceptable for accurate measurement, the examiner clicks on an analysis start key displayed on the viewing screen of the display 24 using the mouse 30. Thus, an analysis is started. An analysis start signal causes the arithmetic-and-control unit 20 to execute an analysis of corneal topography such as the one represented by the flowchart of FIG. 2 and described next.

Figure 2:
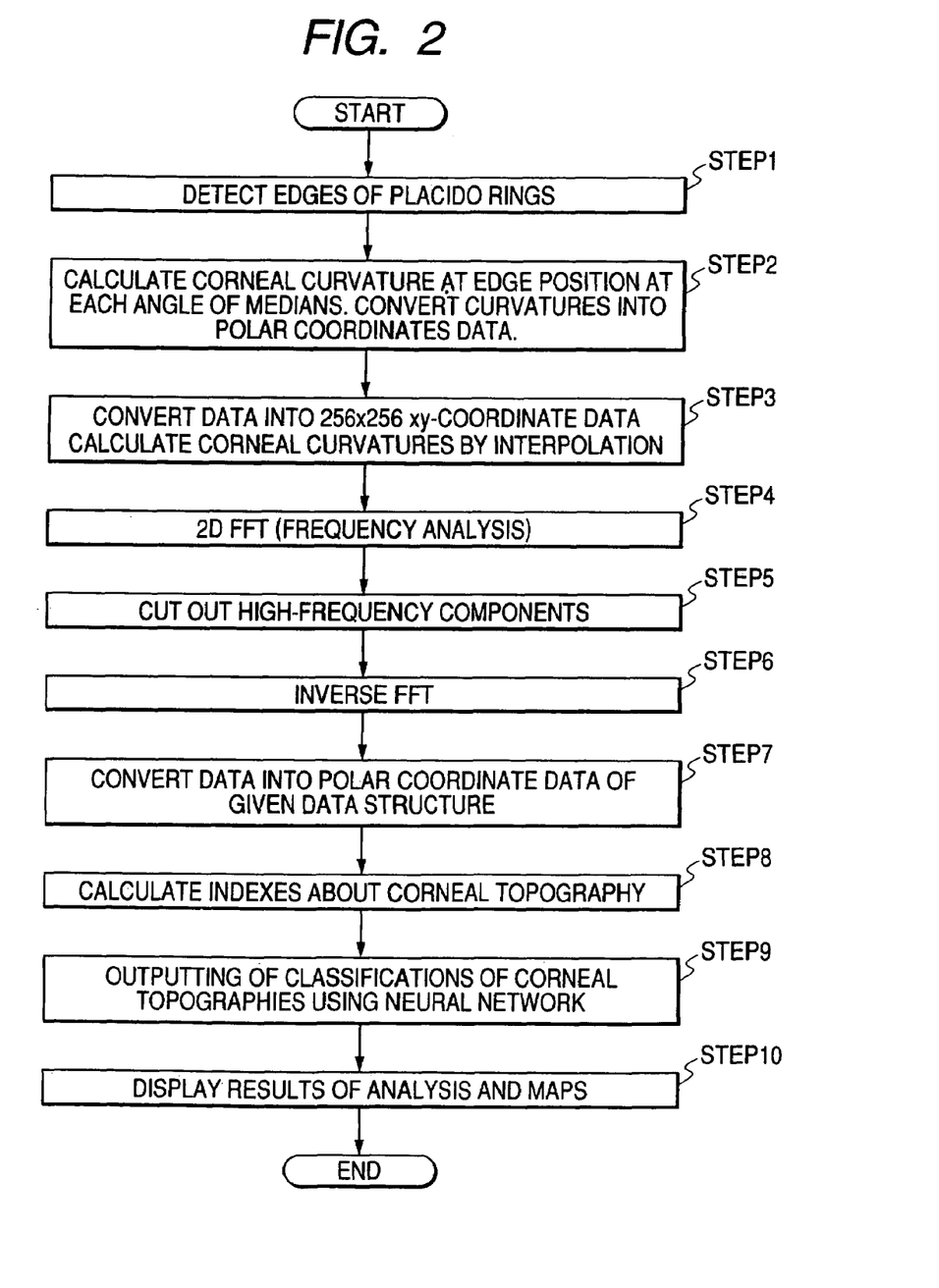
FIG. 2 is a flowchart illustrating analysis of corneal topography.

The arithmetic-and-control unit 20 detects the edges of the boundaries between black and white circles of each Placido ring image as described above (step 1). The arithmetic-and-control unit 20 calculates the corneal curvature (axial curvature) at each given angle based on the distance of each edge from the corneal center (step 2). Details of the method of calculating the corneal curvature are described in JP-A-H7-124113 and U.S. Pat. No. 5,500,697. For example, assume that there are 23 rings to be analyzed and that sampling is done at every one degree of the measuring meridian angle. The corneal curvature of a 23×360 polar coordinate data matrix is obtained. The obtained data for the corneal topography depends on the structures intrinsic to the system and on the method of processing, such as the number of Placido rings, the ring spacing, and the sampling angle. The axial curvature that is one kind of fundamental data indicating the corneal topography contains a slight amount of detection error (or noise) in the stage of detection of the edges of black and white circles of the Placido ring image.

To eliminate the dependence on the structures intrinsic to the system, the following steps are performed. First, the data for the corneal curvature in the form of the polar coordinate data matrix entered (or obtained) as described above is converted into denser orthogonal coordinate data (xy-coordinate data) (step 3). At this time, the value of the corneal curvature at each coordinate is calculated from the corneal curvatures at polar coordinates by interpolation. Various methods can be adopted for the interpolative calculations of corneal curvatures. For example, the space between two edge positions can be simply linearly interpolated. For example, if 23 black and white edge rings exist in an area having a diameter of 12 mm to be subjected to corneal topography analysis (edge spacing equals about 0.52 mm) and form a data structure intrinsic to the system, the data is calculated by interpolation within the same area on the cornea and converted into 256×256 orthogonal coordinates. Assuming that the diameter of the area on the cornea is 12 mm, a 256×256 data matrix is produced at a spacing of 0.047 mm on the cornea.

Figure 3A:
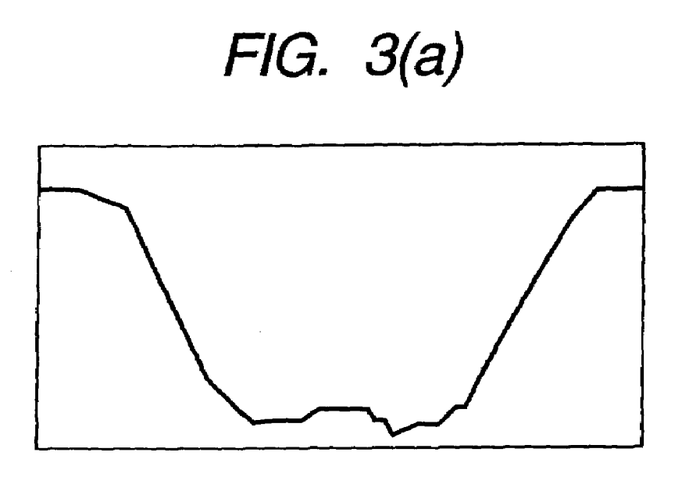
FIG. 3 shows graphs of data for corneal curvatures before and after noise removal and smoothing processing.
Figure 3B:
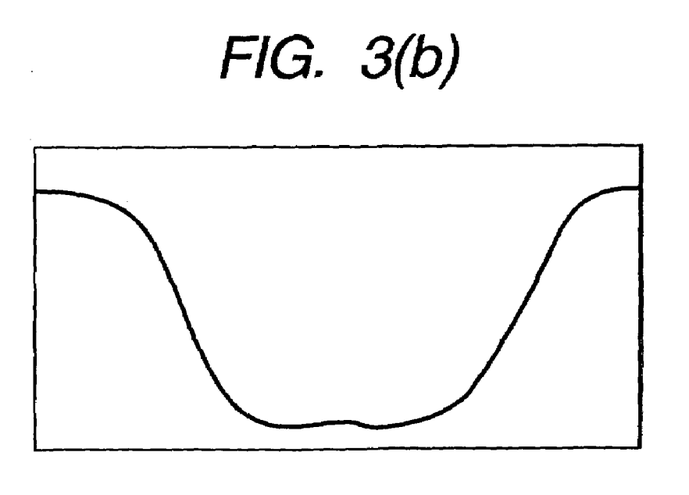

Then, the orthogonal coordinate data matrix is subjected to two-dimensional fast Fourier transform (2D FFT) and converted into frequency domain data (step 4). After removing certain high-frequency components (step 5), an inverse Fourier transform (IFT) is performed (step 6). This results in smoothed corneal curvature data from which high-frequency component noises have been removed. FIG. 3a is a graph of the corneal curvature data for the horizontal (X-axis) coordinates in the stage of interpolation calculation after conversion into the orthogonal coordinate data in step 3. In contrast, FIG. 3b is a graph of corneal curvature data obtained after the execution of the inverse Fourier transform in step 6. It can be seen that noise removal and smoothing have been performed. The frequency analysis is not limited to FFT. Other frequency analysis techniques such as wavelet transform techniques may be used.

The inverse Fourier-transformed orthogonal coordinate data are reconverted into a polar coordinate data matrix (step 7). This polar coordinate data matrix may be converted into a given data structure convenient for calculations of indexes characterizing the corneal topography and for map representation. For example, the data structure is returned to the coordinates of the edge positions of 23 rings and measuring meridians spaced from each other by 1° such that the existing analysis and display routines about map representations can be applied. Alternatively, a new data structure in which measuring meridians spaced from each other by 1° and a given spacing of about 0.1 to 0.2 mm are used may be created. In this case, data arrays are regularly spaced and so data calculation about the area on the cornea is facilitated. For instance, where corneal powers on strong and weak principal meridians at radial positions of 3 mm, 5 mm, and 7 mm on the cornea are found and displayed, it is only necessary that the corresponding data be specified and a calculation be performed. Furthermore, the memory capacity can be saved compared with the case where data decompressed into 256×256 orthogonal coordinate data items are directly stored. Moreover, the time required for subsequent data computation can be shortened.

By adding the steps 3 to 7 described thus far to the related art method, a data structure not dependent on the structures and processing intrinsic to the system such as the number of Placido rings can be achieved. Calculations of various indexes regarding the corneal topography as described below and calculations for display of the results of the analysis are made possible by a common routine.

Analysis regarding judgment of the classifications of corneal topographies is described next. On the basis of the corneal curvature data obtained by step 7 described above, several indexes are calculated. For example, the following 18 indexes are calculated: SIMK1 (Simulated K1), SIMK2 (Simulated K2), MINK (Minimum Keratometry Value), SRI (Surface Regularity Index), SRC (Area compensated Surface Regularity Index), OSI (Opposite Sector Index), DSI (Differential Sector Index), CSI (Center/Surround Index), KPI (Keratoconus Prediction Index), CYL (Simulated Keratometric Cylinder), IAI (Irregular Astigmatism Index), ACP (Average Corneal Power), FAA (Analyzed Area), CEI (Corneal Eccentricity Index), KCI (Keratoconus Index), CVP (Coefficient of Variation of Corneal Power), SDP (Standard Deviation of Corneal Power), SAI (Surface Asymmetry Index) (step 8).

SIMK1 and SIMK2 are powers on strong and weak principal meridians at a radial position of about 3 mm on the cornea. Numerical values higher than the normal value predict keratoconus, cornea-transplanted eyes, and natively steep corneas. Numerical values lower than the normal value predict myopia-corrected corneas and natively flat corneas.

MINK is the lowest power of the powers at a radial position of 3 mm on the cornea. In some corneas with irregular astigmatism, strong and weak principal meridians are not present in 90 degree directions. This will become an important factor during surgery for correction of astigmatism. Such irregular astigmatism is seen on eyes with keratoconus, cornea-transplanted eyes, impaired eyes, and eyes that have undergone cataract surgery.

SRI indicates a local variation in the center of the cornea and is a value associated with PVA (potential visual acuity). An increase in SRI means that the corneal surface within the pupil radius is irregular. Dry eyes, corneal deformation due to wearing of contact lenses, impaired eyes, and cornea-transplanted eyes indicate high values. SRC is an index obtained by correcting SRI by the area of the subject to be analyzed. SRI is calculated by the following formula.

$$SRI = \ln\left[\frac{A \cdot \sum_{i=2,10}^{j=1,360} B \times \left|P_{i,j} - \frac{(P_{i+1,j} + P_{i-1,j})}{2}\right|}{N}\right] - C$$

where i the ring number, j is the position on a meridian, A is a constant, B is a constant, C is a constant, and N is the number of measuring points.

ACP is the average corneal power within the entrance pupil. This can be regarded as the SE value of the cornea. If the keratometry value is abnormal, ACP also takes an abnormal value.

CEI means eccentricity indicating asymmetry of the cornea. A positive (+) value indicates a prolate cornea. 0 (a nil value) indicates a spherical cornea. A (−) negative value indicates an oblate cornea. A keratoconus shows a positive value much higher than those of normal corneas. Corneal deformation due to wearing of contact lenses (CL) and myopia corrected eyes show negative (−) values. CEI is calculated by the following formula.

$$CEI = \frac{\sum_{i=1,23} e_i}{N}$$

where i is the ring number, $e_i$ is the eccentricity calculated from the average distance from the center of the cornea at the ith ring and from the height (distance from the corneal vertex plane to the ith ring), and N is the number of measuring points.

CVP is a numerical value indicative of an index created from the power distribution over the whole region on the cornea and calculated from the following formula.

CVP=1000×(standard deviation SD of powers over
the whole region on cornea/average power over
the whole region on cornea)

Where the value of the CVP is high, the cornea shows a multifocal nature. For example, this is seen on keratoconi of moderate to heavy degree. Furthermore, it is seen during or after a cornea transplant surgery.

With respect to OSI, DSI, CSI, IAI, FAA, SAI, and KPI, they are described by Maeda N., Klyce SD, Smolek MK, and Thomson HW in "Automated Keratoconus Screening With Corneal Topography Analysis, Invest Ophthalmol Vis. Sci., 1994; 35: 2749-2757" (Reference 2), which is incorporated herein by reference.

Figure 4:
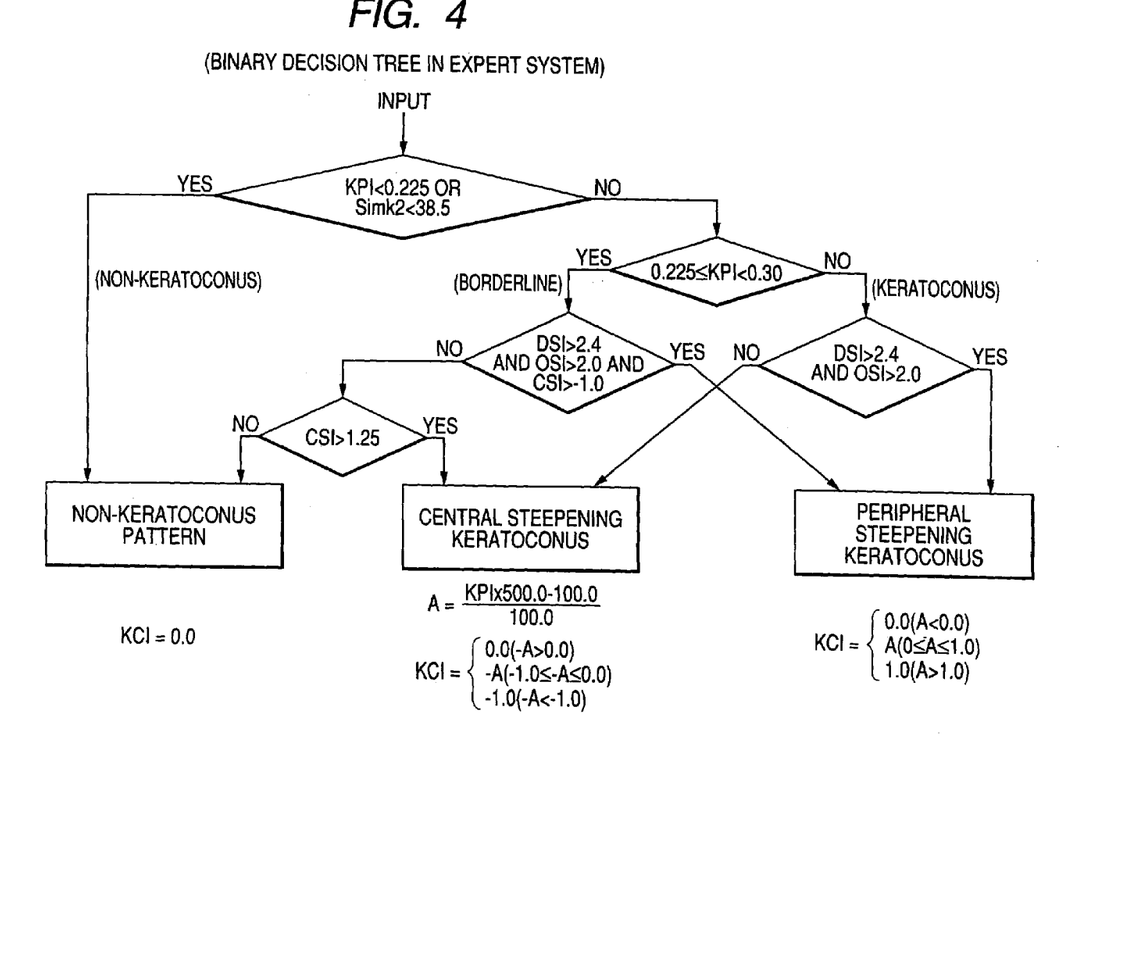
FIG. 4 is a diagram illustrating a method of calculating the keratoconus index (KCI).

KCI is an index evaluating a similarity to keratoconus. KCI is found by the method illustrated in FIG. 4. The method of FIG. 4 is described as an expert system classifier in Reference 2 above. The KPI (Keratoconus Prediction Index) in the figure is described in Reference 2, which is incorporated herein by reference.

Figure 5:
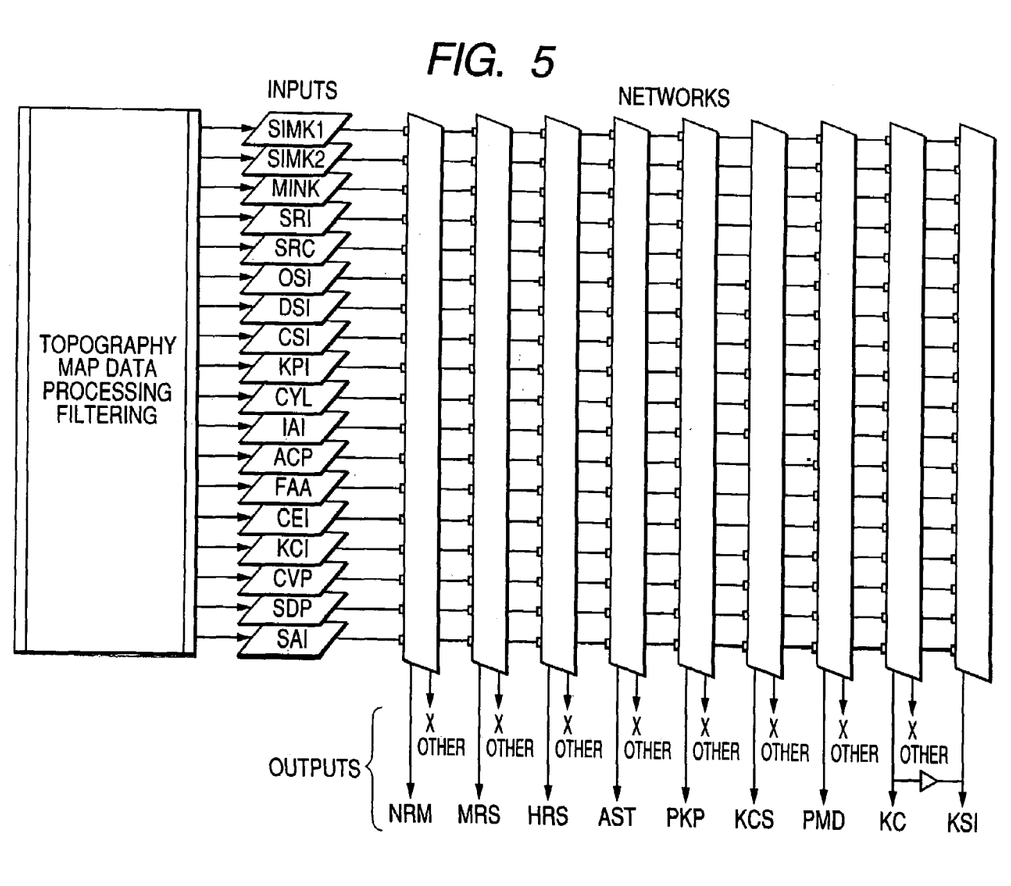
FIG. 5 is a block diagram of a neural network for judging the classifications of corneal topography.

These 18 indexes are taken as input data, and the probability (%) of the classification of each of various corneal topographies is output using a neural network (step 9). FIG. 5 is a block diagram of the network for judging the classification of each corneal topography. In this example, the corneal topographies are classified into known classifications (i.e., NRM (normal cornea), MRS (myopic refractive surgery), HRS (hyperopic refractive surgery), AST (corneal astigmatism), PKP (penetrating keratoplasty), KCS (keratoconus suspect), PMD (pellucid marginal degeneration), and KC (keratoconus)) and OTH (other known or unknown classifications), i.e., 9 classifications in total. There is also provided a KSI (keratoconus severity index) output for evaluating the severity of KC if the result of the decision is KC.

The probability of each classification of each of the corneal topographies is determined using a neural network (step 9) in combination with an expert system. The unaccounted for probability in the neural network process is represented by the OTH classification.

The decisions of the classifications of the corneal topographies and their probabilities can be found as described next by entering the 18 indexes into the neural network.

A total of 1825 OPD-Scan® topography maps were acquired that encompassed the 8 classifications: normal, astigmatic, keratoconus suspect, keratoconus, pellucid marginal degeneration, penetrating keratoplasty, and hyperopic and myopic refractive surgery. These topography maps were clinically classified into one of the 8 corneal topography classifications. These maps were then reviewed and judged again by human experts in manual analysis of corneal topography for correctness of the classification and for the severity of keratoconus, if present. After review by the expert human corneal topography graders, 224 maps were chosen for neural network training and another 224 maps were selected at random for testing. The remaining maps were not considered prime examples of the 8 different classifications and were not used for training or testing. Each classification contained approximately 28 maps in both the training and test sets. Selection of training maps was based on image quality and the existence of features deemed typical for each classification. When KC was judged as being present, the human experts also assigned a KSI value for the purpose of training and testing the ability of the network to grade the severity of keratoconus.

Each map was Fourier-filtered to a common resolution and 18 corneal indexes extracted for use as neural network inputs (SimK1, SimK2, MinK, CYL, SRI, SRC, OSI, DSI, CSI, SAI, CEI, IAI, ACP, AA, SDP, CVP, KPI, & KCI). These corneal indexes were previously shown to be sensitive to various topographical features. While 18 indexes are used as inputs into the total network, it was determined during network training that some of the individual networks that comprise the total network must use fewer inputs to correctly make a decision. Specifically, as shown in FIG. 5, the PKP network does not use KCI as an input and the KCS network does not use SIMK1, SIMK2, MINK, SRI, SRC, ACP, IAA, and CEI as inputs (FIG. 5).

Figure 6:
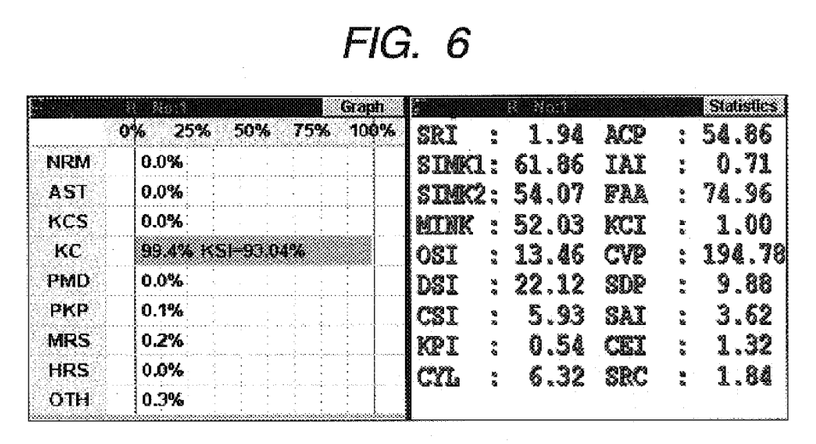
FIG. 6 represents an example of display of the results of analysis of classifications of corneal topographies.

With the exception of the Keratoconus Severity Index (KSI) network which had only one output graded from a severity ranking of 0 (no sign of KC) to 1 (maximum KC severity), each of the individual networks has two numerical outputs ranging between 0 (no response) to 1 (the maximum level of the condition seen in the training set examples) for each category. The first output is the desired classification and the second output is called "Other". Information in the first output is used for classification, while the information in the "Other" output is discarded, as indicated by the symbol "X" in FIG. 5). These "Other" outputs are used to make the networks train faster and more reliably. When the classification output value approaches 0, the network is indicating a total lack of similarity of the input variables to the input data originally used to train the network for that classification. When the classification output value approaches 1, the network is indicating a high degree of similarity of the input variables to the original training data for that classification. Finally, the output value is converted into a percentage, so that the graphical display output (as shown in FIG. 6) ranged from 0% to 100%. This percentage indicates the similarity, and therefore the likelihood or probability of the analyzed topography pattern of the tested cornea matching one or more of the classifications or the keratoconus severity index (KSI) learned by the neural networks.

Each of the individual networks was designed using a back-propagation, feed-forward neural network training process with a single hidden layer in which the network output was compared to the desired outcome specified in the training set. The single hidden layer contained the same number of neurons as the number of inputs (e.g., 18 or fewer, depending on the category). If the output error was greater than the desired tolerance during training, the internal weighting parameters of the network matrix of neurons was systematically adjusted until an acceptable answer was found for all training examples. In addition, the network was tested simultaneously with an independent data set after each training run through all training example maps. As the individual networks improved in the ability to correctly classify both the training and test set examples, the acceptable error tolerance in both the training and testing regimens was systematically set lower in order to achieve an even higher accuracy. When the individual network reached the maximum number of correct responses with the independent test set and no further training lead to an improvement with the test set, training was considered complete. This training process was repeated for all 8 classification networks and for the keratoconus severity index network. The specific levels of accuracy that was achieved with the independent test set data are shown in the following Table 1:

TABLE 1

| Category | Accuracy |
| --- | --- |
| KSI | 94% |
| KC | 97% |
| KCS | 94% |
| PMD | 96% |
| MRS | 98% |
| HRS | 99% |
| AST | 96% |
| NRM | 96% |
| PKP | 94% |

The final neural network matrices that are used to define the knowledge acquired by the trained neural network are arrays of weighting coefficients. These coefficients are those applied at each neuron interconnection within the network. The mean output of each individual network can be described by a simple linear equation which indicates the relative strength and sign of each input term toward determining the appropriate classification. In other words, each equation is an expression of the mean sum of the weighted coefficients of each index within the training set. These equations are shown in FIG. 8.

Once the neural network outputs are found for all categories, the results are passed through an expert system threshold filter to obtain the final classification score. The threshold at which a result is displayed on the bar graph shown in FIG. 6 is adjustable. Currently the threshold is set to 10% or a 0.10 output response value from each of the classification networks. Maps classified as significant for the KC category will also trigger the display of the KC severity in the form of the KSI network output, (as indicated by the control shown in FIG. 5). If the KC output is not above 10%, the corresponding KSI severity index is not displayed.

FIG. 6 gives an example of the result of the analysis of classifications of corneal topographies displayed on the display 24. The indexes found from corneal curvature data and their values are displayed on the right half of the display screen. The probabilities of the items of the classifications of the corneal topographies are graphically represented on the left half of the display screen, together with their numerical values. Since the probabilities of the various topographies are graphically represented, it is easy to understand the contents visually. The diagnosis is also facilitated. KSI is given in terms of a numerical value when KC is more than a predetermined percentage, such as 50%. Since MRS, HRS, AST, PKP, and so on are classified together with KC and KSI regarding keratoconus, it is possible to judge the optimal visual aid (spectacles or contact lenses) for the eye. Also, the decision as to whether refractive surgery should be applied can be made precisely.

Figure 7:
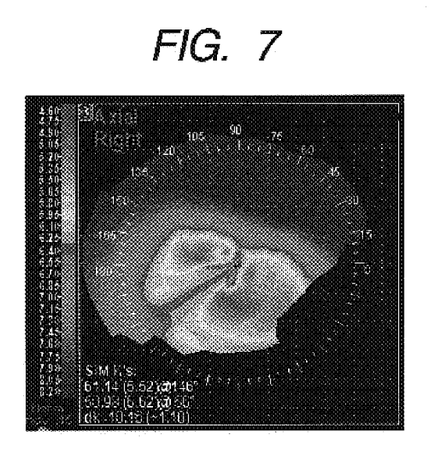
FIG. 7 represents an example of a display of a color map showing the distribution of corneal curvatures.

FIG. 7 shows an example of a display of a color map of the distribution of corneal curvatures. When a corneal topography is diagnosed, the diagnosis is made more precise by observing the distribution of corneal curvatures at the same time. For the display of the color map, the polar coordinate data calculated in step 7 in the flowchart of FIG. 2 are used. The structural dependence intrinsic to the system has been removed. The display program can be made common to topography devices with different Placido ring numbers.

In the structure according to the embodiment described so far, an analyzing function is imparted to the measuring system having the corneal topography measuring optical system. The cornea analysis function subsequent to step 3 in FIG. 2 may be assigned to the computer 40. In this case, the corneal curvature data found by the arithmetic-and-control unit 20 are sent to the computer 40 from the communication port 33. The computer 40 has a function of entering the corneal curvature data.

The above description of the preferred embodiments has been given by way of example. From the disclosure given, those skilled in the art will not only understand the present invention and its attendant advantages, but will also find apparent various changes and modifications to the structures disclosed. It is sought, therefore, to cover all such changes and modifications as fall within the spirit and scope of the invention, as defined by the appended claims, and equivalents thereof.

What is claimed is:

1. A corneal topography analysis system comprising:
an input unit for inputting corneal shape data of an eye to be examined;
an analysis unit that determines plural indexes characterizing topography of the cornea (corneal topography) based on the input corneal shape data, the analysis unit further judges corneal topography of the eye, including keratoconus (KC), keratoconus suspect (KCS) and pellucid marginal degeneration (PMD), using the determined indexes and a neural network; and
a display unit that displays a judging result of the corneal topography by the analysis unit,
wherein the neural network is trained so as to input corneal topography having been clinically judged in advance, including keratoconus, keratoconus suspect and pellucid marginal degeneration, determine weighted coefficients for each corneal topography and output the judging result of the corneal topography.

2. A corneal topography analysis system comprising:
an input unit for inputting corneal shape data of an eye to be examined;
an analysis unit that determines plural indexes characterizing topography of the cornea (corneal topography) based on the input corneal shape data, the analysis unit further judges corneal topography of the eye, including keratoconus (KC), keratoconus suspect (KCS) and pellucid marginal degeneration (PMD), using the determined indexes and a neural network; and
a display unit that displays a judging result of the corneal topography by the analysis unit,
wherein said analysis unit converts the corneal shape data entered by the input unit into data in the form a denser first data matrix by interpolation, removes high-frequency components from the converted data by frequency analysis, and converts the resulting data into data in the form of a given second data matrix.

3. The corneal topography analysis system of claim 2, wherein said analysis unit removes the high-frequency components from the converted data by fast Fourier transform (FFT) and smoothes the resulting data by inverse FFT.

4. The corneal topography analysis system of claim 2, wherein the corneal curvature data entered by the input unit is data in the form of a polar coordinate data matrix, and wherein said analysis unit converts the corneal shape data into data in the form of an orthogonal coordinate data matrix as the first data matrix, removes the high-frequency components from the converted data by fast Fourier transform (FFT), smoothes the resulting data by inverse FFT, and converts the smoothed data into data in the form of a polar coordinate data matrix as the second data matrix.

5. A corneal topography analysis system comprising:
an input unit that enters corneal shape data of an eye to be examined; and
an analysis unit that converts the corneal shape data into data in the form of an orthogonal coordinate data matrix as a denser first data matrix by interpolation, removes high-frequency components from the converted data by fast Fourier transform (FFT), smoothes the resulting data by inverse FFT, converts the smoothed data into data in the form of a polar coordinate data matrix as a given second data matrix, and judges corneal topography of the eye based on the converted data.

6. A method of analyzing corneal topography of a cornea comprising the steps of:
obtaining corneal shape data of an eye to be examined;
determining plural indexes characterizing topography of the cornea (corneal topography) based on the obtained corneal shape data; and
judging corneal topography of the eye, including keratoconus (KC), keratoconus suspect (KCS) and pellucid marginal degeneration (PMD), using the determined indexes and a neural network; and
displaying a judging result of the corneal topography by the analysis unit,
wherein the neural network is trained so as to input corneal topography having been clinically judged in advance, including keratoconus, keratoconus suspect and pellucid marginal degeneration, determine weighted coefficients for each corneal topography and output the judging result of the corneal topography.

7. A method of analyzing corneal topography of a cornea comprising the steps of:
obtaining corneal shape data of an eye to be examined;

converting the obtained corneal shape data into data in the form of an orthogonal coordinate data matrix as a denser first data matrix by interpolation;

removing high-frequency components from the converted data by fast Fourier transform (FFT);

smoothing the resulting data by inverse FFT;

converting the smoothed data into data in the form of a polar coordinate data matrix as a given second data matrix; and judging corneal topography based on the converted data.

8. The corneal topography analysis system according to claim 1, wherein the corneal topography to be judged by the analysis unit further includes corneal subjected to myopic refractive surgery (MRS) and corneal subjected to hyperopic refractive surgery (HRS), and the neural network is trained so as to input corneal topography having been clinically judged in advance, including corneal subjected to myopic refractive surgery and corneal subjected to hyperopic refractive surgery, determine weighted coefficients for each corneal topography and output the judging result of the corneal topography.

9. The corneal topography analysis system according to claim 1, wherein the corneal topography to be judged by the analysis unit further includes at least one of normal cornea (NRM), corneal astigmatism (AST) and penetrating keratoplasty (PKP), and the neural network is trained so as to input corneal topography having been clinically judged in advance, including at least one of normal cornea (NRM), corneal astigmatism (AST) and penetrating keratoplasty (PKP), determine weighted coefficients for each corneal topography and output the judging result of the corneal topography.

10. The corneal topography analysis system according to claim 1, wherein the plural indexes to be determined by the analysis unit includes at least one of minimum keratometry value (MINK), average corneal power (ACP) and corneal eccentricity index (CEI).

11. The corneal topography analysis system according to claim 1, wherein the plural indexes to be determined by the analysis unit includes minimum keratometry value (MINK), surface regularity index (SRI), area compensated surface regularity index (SRC), opposite sector index (OSI), differential sector index (DSI), center/surround index (CSI), keratoconus prediction index (KPI), simulated keratometric cylinder (CYL), irregular astigmatism index (IAI), average corneal power (ACP), analyzed area (IAA), corneal eccentricity index (CEI), keratoconus index (KCI), coefficient of variation of corneal power (CVP), standard deviation of corneal power (SDP) and surface asymmetry index (SAI).

* * * * *